United States Patent [19]

Kropfgans et al.

[11] Patent Number: 5,616,762
[45] Date of Patent: Apr. 1, 1997

[54] PROCESS FOR THE PREPARATION OF 3-HALO-AND PSEUDOHALO-ALKYLSILANE ESTERS

[75] Inventors: Frank Kropfgans; Albert Frings; Michael Horn; Hans-Joachim Koetzsch; Jaroslaw Monkiewicz; Claus-Dietrich Seiler, all of Rheinfelden; Hans-Guenther Srebny, Duelmen-Rorup; Burkhard Standke, Loerrach, all of Germany

[73] Assignee: Huels Aktiengesellschaft, Marl, Germany

[21] Appl. No.: 548,131

[22] Filed: Oct. 25, 1995

[30] Foreign Application Priority Data

Oct. 25, 1994 [DE] Germany ............ 44 38 031.3
Sep. 20, 1995 [DE] Germany ............ 195 34 853.2

[51] Int. Cl.$^6$ ............ C07F 7/08; C07F 7/10
[52] U.S. Cl. ............ 556/479; 556/414; 556/415; 552/4
[58] Field of Search ............ 556/479, 415, 556/414; 552/4

[56] References Cited

U.S. PATENT DOCUMENTS 3,296,291  1/1967  Chalk et al. .
3,564,266  2/1971  Klotz, Jr. .
4,658,050  4/1987  Quirk .
5,523,436  6/1996  Dauth et al. ............ 556/479

OTHER PUBLICATIONS

Tanaka M. et al, "Ruthenium Complex–Catalyzed Hydrosilylation of Allyl Chloride with Trimethoxysilane", Chemical Abstracts, vol. 119, No. 17, Oct. 25, 1993, p. 802.

Kopylova, L.I. et al, "Iridium Complexes in the Hydrosilylation of Unsaturated Compounds", Russian Journal of General Chemistry, vol. 63, No. 10, Oct. 1993, pp. 2257–2266.

Belyakova Z. V. et al, "Patterns of Behavior in the Reactions of Hydride Silanes with Allyl Chloride", Zhurnal Obshchei Khimii, vol. 44, No. 11, Nov. 1974, pp. 2439–2442.

*Primary Examiner*—Paul F. Shaver
*Attorney, Agent, or Firm*—Oblon, Spivak, McClelland, Maier & Neustadt, P.C.

[57] ABSTRACT

3-Halo- and pseudohalo-alkylsilane esters are prepared by reacting an allyl X compound or a compound containing an allyl X structure with a hydridosilane ester in the presence of an iridium catalyst prepared under specific conditions and/or the reaction medium containing a 0.01–100 mol % excess of the allyl X compound or compound containing the allyl X unit relative to the amount of hydridosilane ester reactant.

9 Claims, No Drawings

PROCESS FOR THE PREPARATION OF 3-HALO-AND PSEUDOHALO-ALKYLSILANE ESTERS

BACKGROUND OF THE INVENTION

Field of the Invention

The invention relates to a process for the preparation of 3-halo- and pseudohalo-alkylsilane esters by addition of hydridosilane esters in the presence of catalysts to the double bond of unsaturated aliphatic compounds which contain, as reacting group, the allyl halide or pseudo-halide structural element with a terminal double bond.

3-Chloropropyltrialkoxysilane, Si-methyl-3-chloropropyldialkoxysilane and Si,Si-dimethyl-3-chloropropylalkoxysilane in particular are used as silane coupling agents, for example for glass fibres, in the foundry industry and as fillers for polymers. The 3-halo- or pseudohalo-alkylsilane esters of formula I in particular are important key products for the preparation of, for example, a variety of mercapto-, amino-, methacryloyloxy- and acryloyloxy-functional organosilanes, which have grown in importance over recent years to become a branch of industry in their own right.

Consequently there have already been attempts in various ways to prepare such products. Current industrial production exclusively employs a two-stage procedure in which allyl chloride is hydrosilylated with trichlorosilane or methyldichlorosilane, generally in the presence of platinum-based catalysts, with the respective chloropropylchlorosilane, which is obtained in yields of between 50 and 83%, being subsequently esterified.

These production processes which are currently practiced are highly material- and plant-intensive but, despite their considerable disadvantages, have to be employed given the lack of better alternatives, since the products are urgently required.

For this reason it has already been proposed, to hydrosilylate allyl chloride using trialkoxysilanes. This method employs various platinum catalysts and it is possible to realize product yields from about 20 to 45%. The reproducibility of certain yields, which are indicated as being up to about 70%, is disputed. Belyakova et al, Zh. Obshch. Khim. 44 (106) 1974, No. 11, 2439–2442, report on the detailed investigation of this reaction path employing platinum catalysis. Moreover, they describe the secondary reactions which occur and confirm product yields ranging from about 20 to 45%. In the presence of rhodium catalysts using the methods described in U.S. Pat. Nos. 3,296,291 and 3,564,266, the product yields are again below 40% and are accompanied by considerable secondary reactions. In the presence of high concentrations of specific dimeric iridium-halide-diene complex catalysts, in accordance with U.S. Pat. No. 4,658,050, the yields determined by gas chromatography reach levels of 75%; however, in preparative terms it is only possible to achieve product yields of 55–60%. Further, the by-products described by Belyakova et al occur in large amounts too. A striking additional disadvantage is the need to use such costly noble metal complexes in a high concentration. Leaving aside the cost factor, this also leads to intolerable impurity and waste problems. A need, therefore, continues to exist for a simple method of preparing 3-halo and pseudohalo-alkylsilane esters at improved yields at reasonable cost.

SUMMARY OF THE INVENTION

Accordingly, one object of the present invention is to provide a simple method of preparing 3-halo and pseudohaloalkylsilane esters in improved yields at reasonable cost.

Briefly, this object and other objects of the present invention, as hereinafter will become more readily apparent, can be attained in a method of preparing 3-halo- and pseudohalo-alkylsilane esters of formula (I):

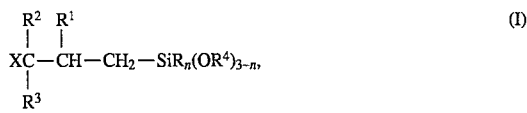

wherein
R is an alkyl, a branched alkyl or a cycloalkyl group having 1 to 18 carbon atoms, which may be halogenated;
$R^1$ is R or hydrogen;
$R^2$ is R, hydrogen, an aryl substituent or halogen;
$R^3$ is the same as group $R^2$, with the $R^3$ substituent being the same as or different from the specific $R^2$ group selected;
$R^4$ is a branched or unbranched alkyl group of 1 to 10 carbon atoms, optionally containing aliphatic ether groups;
X is a fluoride, chloride, bromide, iodide, cyanide, isocyanate, isothiocyanate or azido radical; and
n is 0, 1 or 2 by hydrosilation, which comprises: reacting a compound of formula (II):

wherein X, $R^1$, $R^2$ and $R^3$ are as defined above, or a compound containing the pseudohalide structure of formula (II) as a component, wherein one of $R^2$ or $R^3$ represents a bond to a carbon atom of the remaining portion of the compound, with a hydridosilane ester of formula (III):

wherein R, $R^4$ and n are as defined above, in the presence of a catalyst of a group VIII element or compound thereof in a reaction medium under the conditions in which (i) the amount of compound of formula (II) or compound containing formula (II) is present in a 0.01 to 100 mol % excess of the amount of compound of formula III and/or (ii) the catalyst is prepared by stirring a 1/10 to 1/10,000 molar solution of elemental Ir, a compound of Ir or a combination thereof in the reaction medium without heating for at least 20 minutes, the catalyst having a concentration of from $10^{-5}$ to $10^{-3}$ mol %, based on the hydridosilane ester employed, and then conducting the hydrosilation reaction.

DETAILED DESCRIPTION OF THE PREFERRED EMBODIMENTS

It has surprisingly now been found that the difficulties in synthesis of 3-halo and pseudohaloalkylsilane esters can largely be avoided, and that ester products can be obtained in yields of up to 89% if, for the preparation of the products of formula I by the catalyzed hydrosilylation of unsaturated aliphatic compounds, which contain as the reacting group allyl halide or a pseudohalide structural element having a terminal double bond, each of formula II:

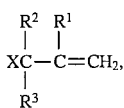

(II)

wherein X, $R^1$, $R^2$ and $R^3$ as defined above, with hydridosilane esters having the structure III:

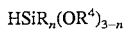

(III), wherein R, $R^4$ and n are as defined above, (i) the reaction is conducted in the presence of elements and/or compounds from subgroup VIII of the Periodic Table, where the reaction component of formula II, alone or in a mixture, always is in excess of from 0.01 to 100 mol %, preferably from 0.1 to 10 mol %, relative to the reaction component of formula III, if desired in a from 5 to 95% strength by weight solution in an inert solvent (suitable solvents include hydrocarbons), and/or (ii) the ester product of formula I, at from one-tenth to ten-thousandth molar solution or suspension of elemental iridium and/or of compounds of iridium, is prepared by stirring for at least 20 minutes in the presence of a catalyst at a concentration of from $10^{-5}$ to $10^{-3}$ mol %, based on the hydrogensilane employed. The hydrosilylation can be carried out in a manner known per se.

For example, in a batchwise process the reaction components of formula III are introduced into the reactor as an initial charge, preheated to, for example, 70° C. and doped with the catalyst solution prepared in accordance with the invention, and finally the reactant of formula II is metered in with stirring, all the while controlling the exothermicity of the reaction. The reaction time to be employed is generally from 30 to 180 minutes.

In a batchwise process, however, another advantageous mode of reaction is one in which the catalyst is preformed in situ in the mixture of reaction components II and III or with excess II, then, in the latter case, component III is added, and finally the reaction is performed by heating to the activation temperature while controlling the exothermic evolution of heat.

The preferred reaction temperature is from 70° to 130° C. If desired, the application of elevated pressure may be useful, preferably up to 40 bar.

In the case of a continuous reaction procedure it is advantageous to premix the two reaction components of formulas II and III and the catalyst preparation, if desired in the presence of from 20 to 75% by weight, based on the sum of reaction components, of hydrocarbons and/or of the product of formula I as medium, and to pass this mixture in liquid form, employing average retention times of from 10 to 50 minutes, through a reaction tube which is thermostated at from about 70° to 120° C. Both in the batchwise and in the continuous reaction procedure, the present process yields up to 89% of the products of formula I.

The crude products of formula I thus prepared by the present process contain comparatively only few by-products, so that it may be possible to avoid subsequent esterification since workup by distillation provides sufficiently pure products, especially for the use of the ester compounds in the synthesis of aminosilanes.

If, however, it is desired to isolate particularly pure and neutral products of formula I, then it is advisable to carry out a simple subsequent esterification of the crude products, which, because of their preparation, still contain residual acidity, by the work-up methods which are generally known per se for silicon esters, for example by addition of some alcohol to neutralize the acidity, followed finally by filtration.

Products of formula I which can be prepared with particular advantage by the present process in contrast to the prior art procedures are the following compounds:
3-Chloropropyltrimethoxy- and -triethoxysilane,
3-Chloropropylmethyldimethoxy- and -diethoxysilane,
3-Chloropropyldimethylmethoxy- and -ethoxysilane,
3-Chloropropyltris(2-methoxy)ethoxysilane,
3-Chloropropyltris(2-methoxyethoxyethoxy)ethoxysilane,
3-Chloropropyldimethyl-sec-butoxysilane,
3-Chloro-2-methylpropyltrimethoxysilane,
2-Chloromethylbutyltrimethoxysilane,
3-Chloro-2-chloromethylpropylmethyldiethoxysilane,
3-Chloro-2-chloromethylbutyltriethoxysilane,
3-Chloropentyldimethyl(2-ethyl)hexyloxysilane,
3-Fluoropropyltriethoxysilane,
3-Bromopropyltriethoxysilane,
3-Bromo-2-methylbutylmethyldimethoxysilane,
3-Iodopropyltriethoxysilane,
3-Iodo-2-methylpropyltriethoxysilane,
3-Cyanopropyltriethoxysilane,
3-Isocyanatopropyltriethoxysilane,
3-Azidopropyltriethoxysilane,
3,4-Dibromo-2,3-dimethylbutylmethyldimethoxysilane,
3-Bromohexyldimethylethoxysilane,
3-Chloroheptyltrimethoxysilane,
3-Azidoheptyldimethylmthoxysilane,
3,3-Difluoropropyltriethoxysilane,
3,3-Dichloropropyltrimethoxysilane,
3,3-Dichloro-2-methylpropyltrimethoxysilane,
3,3,3-Trifluoropropyltriethoxysilane,
3,3,3-Trichloropropyltrimethoxysilane,
3,3,3-Trifluoro-2-trifluoromethylpropyltriethoxysilane, and
3,3,4,4,4-Pentafluorobutyltriethoxysilane.

Starting materials which are suitable for carrying out the process of the invention and which have the structure of formula II include, in particular, the following compounds:
Allyl fluoride,
Allyl chloride,
Allyl bromide,
Allyl iodide,
Allyl azide,
Allyl cyanide,
Allyl isocyanate,
Methallyl fluoride,
Methallyl chloride,
Methallyl bromide,
Methallyl iodide,
3Chloromethyl-1-butene,
3Chloro-2-methyl-1-butene,
3Bromo-2-methyl-1-butene,
3,4-Dichloro-1-butene,
3,4-Dibromo-1-butene,
3Fluoro-2-fluoromethyl-1-propene,
3Chloro-2-chloromethyl-1-propene,
3Chloro-2-chloromethyl-1-butene,
3Chloro--1-pentene,
3-Chloro-2-methyl-1-pentene,
3,3-Difluoro-1-pentene,
3Chloro-1-hexene,
3Bromo-1-hexene,
3Chloro-1-heptene,
3Azido-1-heptene,
3,4-Dibromo-2,3-dimethyl-1-butene,
4Bromo-3-chloro-3,4,4-trifluoro-1-butene,
3,3-Difluoro-1-propene,
3,3-Dichloro-1-propene,
3,3-Dibromo-1-propene, 3,3-Difluoro-2-methyl-1-propene,
3,3-Dichloro-2-methyl-1-propene,
3,3-Dibromo-2-methyl-1-propene,
3,3-Dichloro-2-methyl-1-butene,
3,4-Dichloro-2-methyl-1-butene,
3,4-Dibromo-1-butene,
3,4-Dibromo-2-methyl-1-butene,
3,3,3-Trifluoro-1-propene,
3,3,3-Trichloro-1-propene,
3-Bromo-3,3-difluoro-1-propene,
3-Chloro-2-trifluoromethyl-1-propene,
3,3,3-Trifluoro-2-trifluoromethyl-1-propene,
3,3,4,4,4-Pentafluoro-1-butene,
3,4-Dichloro-3,4,4-trifluoro-1-butene, and
4-Bromo-3-chloro-3,4,4-trifluoro-1-butene.

Using the starting materials of formula II, alone or in a mixture with the other components of the hydrosilylation reaction, but always with excess component of formula II, iridium and/or its compounds are treated in accordance with the invention and thereby the catalytically active solution or suspension is prepared. Examples of suitable iridium components include iridium black, the particularly preferred chlorides such as iridium(III) chloride, iridium(III) chloride hydrate, iridium(IV) chloride hydrate, hexachloroiridic acid 6-hydrate. Suitable iridium compounds also include iridium(IV) oxide hydrate, potassium hexachloroiridate(IV), potassium hexachloroiridate(III) 3-hydrate, tris(acetylacetonato)iridium(III) and iridium(III) oxalate, and complex compounds of iridium, for example cis-dichlorobis(ethylenediamine)iridium(III) chloride, pentaamminechloroiridium(III) chloride, chlorotris(norbornadiene) iridium(I), chloro-(1,5cyclooctadiene) iridium(I) dimer, chlorocarbonylbis(cyclooctene)iridium(I) dimer, bis(tricarbonylchloroiridium), octachlorooctacarbonyltetrairidium(I,II), dodecacarbonyltetrairidium, 1,5-cyclooctadienebis(methyldiphenylphosphine)iridium hexafluorophosphate, bis(triphenylphosphine)iridiumcarbonyl chloride, hydridochlorotris(triphenylphosphine)iridium(III), dihydridochlorotris(triphenylphosphine)iridium(III) and carbonylhydridotris(triphenylphosphine)iridium.

The hydrogensilane esters of formula III which are employed as hydrosilylating reaction components include triethoxysilane, trimethoxysilane, triisobutoxysilane, hydrogenmethyldiethoxysilane or -dimethoxysilane, hydrogencyclohexyldiisopropoxysilane, and hydrogendimethylethoxy-, -octyloxy- or -2-butoxyethoxysilane.

Having generally described this invention, a further understanding can be obtained by reference to certain specific examples which are provided herein for purposes of illustration only and are not intended to be limiting unless otherwise specified.

EXAMPLE 1

In a thermostat-heatable 4 l multi-necked flask equipped with stirrer, internal thermometer and reflux condenser, 12 mg ($4 \cdot 10^{-5}$ mol) of iridium(III) chloride hydrate was added to a liquid mixture consisting of 625 g (2.6 mol) of 3-chloropropyltriethoxysilane as reaction medium, 625 g (8.17 mol) of allyl chloride and 1250 g (7.6 mol) of triethoxysilane as reaction components, over 40 minutes at room temperature under $N_2$. On subsequent heating, a weakly exothermic reaction commenced at about 70° C. during which the internal reactor temperature rose over the course of about 30 minutes, with reflux becoming continually weaker, to 104° C., and fell back again to 94° C. over the course of a further 15 minutes. The mixture was held at 90° C. with the aid of the thermostat for another 30 minutes.

For work-up, first of all the slight excess of allyl chloride was removed by distillation, subsequently the chloride acidity, formed because of the secondary reaction, which amounted to a total of 0.92 mol, was neutralized with an equimolar mixture of ethanol and triethylamine; the remaining mixture was filtered, and finally the product was purified by vacuum distillation via a column.

A total of 2200 g of 3-chloropropyltriethoxysilane was obtained. After deducting the quantity employed of 625 g, the yield is 1575 g. This amount is a yield of 86% based on the triethoxysilane employed. By-products isolated were about 40 g of propyltriethoxysilane and about 140 g of tetra-ethoxysilane.

EXAMPLE 2

A solution of 14 mg of dihydrogen hexachloroiridate in 2 ml of isopropanol was mixed into a solution of 610 g (7.94 mol) of allyl chloride in 625 g (2.6 mol) of 3-chloropropyltriethoxysilane and the mixture was stirred under inert gas at room temperature for one hour. The reaction mixture, together with 1250 g (7.6 mol) of triethoxysilane, was then metered continuously via a mixing nozzle in the liquid phase into a tubular reactor which is fitted with a jacket and $N_2$-blanketed reflux condenser and is configured as a communicating tube, with an average retention time of from 35 to 40 minutes at 79° C. At the entry site, boiling and vigorous reflux occurred. The crude product emerging in liquid form and the communicating overflow was no longer boiling. Work up was carried out as described in Example 1. 1630 g of 3-chloropropyltriethoxysilane were obtained. This amount corresponds to a yield of 89% based on the triethoxysilane employed.

EXAMPLE 3

In a minilab pressure reactor of the TINYCLAVE type (BUECHI) with a capacity of 25 ml, 4 g of p-xylene, 4.2 g (0.055 mol) of allyl chloride and 8.2 g (0.05 mol) of triethoxysilane were mixed intensively with 0.16 mg ($10^{-3}$ mol %) of chloro-(1,5-cyclooctadiene)iridium(I) dimer at room temperature for one hour. The reaction mixture was then heated at 80° C. for 2 hours in a thermostat. Analysis by gas chromatography gave a product yield of 83% of 3-chloropropyltriethoxysilane.

EXAMPLE 4

(Comparison Example)

In analogy to Example 3, a homogeneous reaction solution of 4 g of p-xylene, 3.8 g (0.05 mol) of allyl chloride (instead of 4.2 g corresponding to 0.055 mol), 8.2 g (0.05 mol) of triethoxysilane and 0.16 mg ($10^{-3}$ mol %) of chloro-(1,5-cyclooctadiene)iridium(I) dimer were reacted without a relatively long mixing or storage time. Analysis by gas chromatography gave a product yield of only 61% of 3-chloropropyltriethoxysilane.

EXAMPLE 5

In analogy to Example 1, a reaction mixture consisting of 585 g (2.6 mol) of 3-chloroisobutylmethyldiethoxysilane, 739 g (8.17 mol) of methallyl chloride and 1022 g (7.6 mol) of hydrogenmethyldiethoxysilane was reacted with 16 mg of chlorocarbonylbis(cyclooctene)iridium(I) dimer. The internal reactor temperature rose during this reaction from 70° C. to 112° C. over the course of about 40 minutes. The after-reaction required about 1 hour. A chloride acidity of 1.04 mol was produced. A total of 1986 g of 3-chloroisobutylmethyldiethoxysilane was obtained. After deducting the 585 g quantity of the silane compound employed in the reaction medium at its start, the yield of the silane is 1400 g. This is a yield of 82% based on the methyldiethoxysilane employed. By-products found were isobutylmethyldiethoxysilane and methyltriethoxysilane.

EXAMPLE 6

In analogy to Example 1 a reaction mixture consisting of 700 g of p-xylene, 803 g (8.1 mol) of allyl mustard oil and 936 g (7.66 mol) of trimethoxysilane was stirred at room temperature for 90 minutes with a solution of 22 mg of dihydrogen hexachloroiridate in 3 ml of isopropanol, and the components were reacted at from 90° to 114° C. over 160 minutes. The mixture was worked up by distillation to give 1539 g (91% yield based on the trimethoxysilane employed) of 3-isothiocyanatopropyltrimethoxysilane

EXAMPLE 7

In analogy to Example 3, a mixture of 3 g of p-xylene, 5.3 g (0.055 mol) of 3,3,3-trifluoro-1-propene and 9.4 g (0.5 mol) of cyclopentyldiethoxysilane was reacted in the presence of 0.1 mg of iridium(III) chloride hydrate, after a mixing time of 70 minutes, at 83° C. over 180 minutes. Analysis by gas chromatography gave a product yield of 77% of 3,3,3-trifluoropropylcyclopentyldiethoxysilane.

EXAMPLE 8

In analogy to Example 1, a reaction mixture consisting of 140 g of p-xylene, 242 g (2 mol) of allyl bromide and 335 g (1.9 mol) of hydrogendimethyl(2-butoxyethoxy)silane was reacted in the presence of 2 mg of iridium(III) chloride hydrate. Work-up by distillation gave 432 g of 3-bromopropyldimethyl(2-butoxyethoxy)silane. This corresponds to a preparative yield of 77%, based on the hydrogendimethylsilane ester employed.

EXAMPLE 9

In analogy to Example 6, a reaction mixture consisting of 640 g of p-xylene, 680 g (8.17 mol) of allyl isocyanate and 1250 g (7.6 mol) of triethoxysilane was reacted at from 76° to 92° C. over the course of 150 minutes. Working up by distillation gave 1350 g of 3-isocyanatopropyltriethoxysilane in addition to the trimer.

EXAMPLE 10

In analogy to Example 1 a reaction mixture consisting of 90 g of p-xylene, 144.6 g (1.04 mol) of 3,4-dichloro-2-methyl-1-butene and 259 g (1 mol) of hydrogenethyldimethoxysilane was reacted in the presence of 1 mg of iridium(III) chloride hydrate. Working up by distillation gave 197 g of 3,4-dichloro-2-methylbutylethyldimethoxysilane. This corresponds to a preparative yield of 76%, based on the hydrogenethylsilane dimethyl ester employed.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for the preparation of a silane compound of formula I:

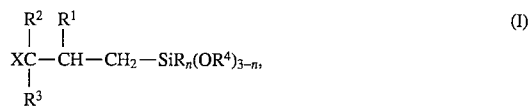

wherein

R is an alkyl, a branched alkyl or a cycloalkyl group having 1 to 18 carbon atoms, which may be halogenated;

$R^1$ is R or hydrogen;

$R^2$ is R, hydrogen, an aryl substituent or halogen;

$R^3$ is equal to $R^2$, with a given $R^3$ substituent being the same as or different from the specific $R^2$ group selected;

$R^4$ is a branched or unbranched alkyl group of 1 to 10 carbon atoms, optionally containing aliphatic ether groups;

X is a fluoride, chloride, bromide, iodide, cyanide, isocyanate, isothiocyanate or azido radical; and n is 0, 1 or 2 by hydrosilation, which comprises: reacting a compound of formula (II):

wherein X, $R^1$, $R^2$ and $R^3$ are as defined above, or a compound containing the pseudohalide structure of formula (II) as a component, wherein one of $R^2$ or $R^3$ represents a bond to a carbon atom of the remaining portion of the compound, with a hydridosilane ester of formula (III):

wherein R, $R^4$ and n are as defined above, in the presence of a catalyst of a group VIII element or compound thereof in a reaction medium under the conditions in which (i) the amount of compound of formula (II) or compound containing formula (II), alone or in a mixture, is present in a 0.01 to 100 mol % excess of the amount of compound of formula III and/or (ii) the catalyst is prepared by stirring a 1/10 to 1/10,000 molar solution or suspension of elemental Ir, a compound of Ir or a combination thereof in the reaction medium without heating for at least 20 minutes, the catalyst having a concentration of from $10^{-5}$ to $10^{-3}$ mol %, based on the hydridosilane ester employed, and then conducting the hydrosilation reaction.

2. The process of claim 1, wherein the amount of compound of formula (II) or compound containing formula (II) is present in 0.1–10 mol % excess relative to the amount of compound of formula (III).

3. The process of claim 1, wherein the compound of formula (II) or compound containing formula (II) is present as a 5–95% strength by weight solution in an inert solvent, in the silane ester product of formula (I) or combinations of the solvent with the silane ester of formula (I).

4. The process of claim 3, wherein said solvent is a hydrocarbon solvent.

5. The process of claim 1, wherein the reaction is conducted at a temperature of 70° to 130° C.

6. The process of claim 1, wherein the reaction is conducted at an elevated pressure.

7. The process of claim 6, wherein the pressure ranges up to 40 bar.

8. The process of claim 1, wherein the reaction is conducted continuously.

9. The process of claim 1, wherein any halosilane or pseudohalosilane compound formed in the reaction as a byproduct is esterified in a known manner.

* * * * *